United States Patent
Padilla-Acevedo et al.

(10) Patent No.: US 11,059,840 B2
(45) Date of Patent: Jul. 13, 2021

(54) SYNTHESIS OF CYCLIC ORGANIC COMPOUNDS AND METALLOCENES

(71) Applicant: Univation Technologies, LLC, Houston, TX (US)

(72) Inventors: Angela I. Padilla-Acevedo, Lake Jackson, TX (US); Roger L. Kuhlman, Lake Jackson, TX (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 16/649,929

(22) PCT Filed: Sep. 19, 2018

(86) PCT No.: PCT/US2018/051616
§ 371 (c)(1),
(2) Date: Mar. 23, 2020

(87) PCT Pub. No.: WO2019/067271
PCT Pub. Date: Apr. 4, 2019

(65) Prior Publication Data
US 2020/0277320 A1   Sep. 3, 2020

Related U.S. Application Data

(60) Provisional application No. 62/564,339, filed on Sep. 28, 2017.

(51) Int. Cl.
| | |
|---|---|
| *C07F 17/00* | (2006.01) |
| *C08F 4/6592* | (2006.01) |
| *C08F 210/16* | (2006.01) |
| *C08F 110/02* | (2006.01) |

(52) U.S. Cl.
CPC .......... *C07F 17/00* (2013.01); *C08F 4/65925* (2013.01); *C08F 110/02* (2013.01); *C08F 210/16* (2013.01)

(58) Field of Classification Search
CPC .... C07F 17/00; C08F 4/65925; C08F 110/02; C08F 210/16
See application file for complete search history.

(56) References Cited

U.S. PATENT DOCUMENTS

| | | | |
|---|---|---|---|
| 5,721,185 A | 2/1998 | LaPointe et al. | |
| 6,911,508 B2 * | 6/2005 | McCullough | C08F 10/00 526/160 |
| 2004/0249096 A1 | 12/2004 | McCullough | |
| 2006/0173123 A1 | 8/2006 | Yang et al. | |

FOREIGN PATENT DOCUMENTS

| | | |
|---|---|---|
| JP | 10316694 | 12/1998 |
| WO | 2018064044 A2 | 4/2018 |

OTHER PUBLICATIONS

Asachenkon, New Zirconocenes with 4,5,6,7-tetrahydroindene ligands. Synthesis and Catalytic activity in the polymerization of ethylene with hex-1-ene, Russian Chemical Bulletin, 2017, vol. 65, No. 6, pp. 1580-1585.

Austin, Synthesis and Properties of Novel Substituted 4,5,6,7-tetrahydroindenes and Selected Metal Complexes, Journal of Organometallic Chemistry, 1995, vol. 491, No. 1-2, pp. 11-18.

Batsanov, Sterically Demanding Cyclopentadienyl Chemistry: Synthesis of Iron and Zirconium Complexes of 1-Phenyl-3-Methyl-4,5,6,7-Tetrahydroindenyl, Journal of Organometallic Chemistry, 1999, vol. 590, pp. 169-179

Conia, Tetrahedron Letters, 1968, vol. 17, p. 2101.

Eaton, Phosphorus Pentoxide-Methanesulfonic Acid. A Convenient Alternative to Polyphosphoric Acid, Journal of Organic Chemistry, 1978, 38, 4071.

Jacob et al, Organic reactions with polyphosphoric acid. VI. Intramolecular acylation with lactones.

Nazarov, 3-Methyl-Tetrahydro-1-Pentalenone Neftekhimiya, 1965, vol. 5, No. 2, p. 177-183.

Paquette, Stereocontrolled Total Synthesis of the Triquinane Marine Sesquiterpene-Capnellene, Canadian Journal of Chemistry, 1984, 62, 2415.

Paquette, Studies Directed Toward the Total Synthesis of Trixkingolide. Analysis of the Capacity for Transannular Carbon-Carbon Bond Formation in Various Bicyclic and Tricyclic Intermediates, J. Org. Chem. 1989, 54, 3334.

Polo, From Zirconium to Titanium: The Effect of the Metal in Propylene Polymerisation using Fluxional Unbridged Bicyclic Catalysts, Macromolecular Sympo, 2004,vol. 213, pp. 89-99.

Rand, Competitive Carbonium Ion Processes. Catalysis of Acylation and Acetoxylation Reactions by Polyphosphoric Acid, Journal of Organic Chemistry, 1966, 31, p. 4061.

(Continued)

*Primary Examiner* — Yong L Chu

(57) ABSTRACT

A method comprising synthesizing a cyclic organic compound via reaction of an unsubstituted or substituted cyclohexene with an unsubstituted or substituted acrylic acid in the presence of phosphoric and/or sulfonic acid reagent to make the cyclic organic compound. Also, a method of synthesizing a ligand for a transition metal, and a related substituted ligand-metal complex and catalyst, from the unsubstituted or substituted cyclohexene and unsubstituted or substituted acrylic acid. Also, the cyclic organic compound, ligand, and substituted ligand-metal complex and catalyst synthesized thereby. Also a method of polymerizing an olefin with the catalyst to give a polyolefin, and the polyolefin made thereby.

9 Claims, No Drawings

(56) References Cited

OTHER PUBLICATIONS

Rand et al., The Acylation of Cycloheptene, Journal of Organic Chemistry, 1966, 31, p. 3063.
Schostarez et al., Highly stereocontrolled synthesis of propellane sesquiterpenes. 1981, vol. 37, No. 25 pp. 4431-4435.
Tabatabaenian, Synthesis and Spectroscopic Studies of New Substituted Dinuclear η5-4,5,6,7-Tetrahydroindenyl Rhuthenium Complexes. Russian Journal of Coordination Chemistry, 2003, vol. 29, No. 7, p. 501.
Brancaccio,Farmaco, Edizione Scientifica, 1983, 9, 702-708.
Yokota, Consideration of Mechanism of Styrene/Ethylene Copolymerization with Half-Titanocene Catalysts, Journal of Polymer Science, 2005, 43, 5041.
Yoshio, Kenkyu Hokoku-Asahi Garasu Kogyo Gijutsu Shoreikai, 1986, vol. 49, 225-230.
Yoshio, Degradation of Polyethylene to Aromatic Hydrocarbons over metal-supported activated carbon catalysts, Journal of Analytical and Applied Pyrolysis, 1989, 14(4), 331-344.
Ouellette, Conformational Analysis. VIII.1,2 Relative Stabilities of 5-Cyanobicyclo[2.2.2]octenes and 5-Acetylbicyclo [2.2.2]octenes, 1966, p. 3065.

* cited by examiner

SYNTHESIS OF CYCLIC ORGANIC COMPOUNDS AND METALLOCENES

FIELD

Synthesizing cyclic organic compounds, and substituted metallocenes therefrom.

INTRODUCTION

Metallocene complexes comprise a transition metal atom that is bonded to two ligands independently selected from an unsubstituted cyclopentadienyl (Cp) ligand (formally an anion of formula $C_5H_5$) and/or a substituted cyclopentadienyl ligand, which is isolobal to Cp. The transition metal is an element of any one of Groups 3 to 12 useful for catalyzing polymerizations of olefins. Examples of the transition metal are Group 4 metals such as titanium, zirconium, and hafnium. Examples of the substituted cyclopentadienyl ligands are methylcyclopentadienyl and 4,5,6,7-tetrahydroindenyl. A typical metallocene complex is a 4,5,6,7-tetrahydroindenyl-cyclopentadienyl zirconium dimethyl complex (((4,5,6,7-tetrahydroindenyl)(cyclopentadienyl)Zr$(CH_3)_2$). Typically, the synthesis of the complex involves numerous synthetic steps, uses expensive reagents, and/or employs a platinum-catalyzed hydrogenation step to convert an indenyl-cyclopentadienyl zirconium dichloride compound to a 4,5,6,7-tetrahydroindenyl-cyclopentadienyl zirconium dichloride compound. See, e.g., US 2004/0249096 A1 and U.S. Pat. No. 5,721,185.

Uemichi, Yoshio; Kanoh, Hisao. *Kenkyu Hokoku-Asahi Garasu Kogyo Gijutsu Shoreikai*, Volume 49, Pages 225-30, 1986. CODEN:AGKGAA. ISSN:0365-2599 report that platinum is especially potent source of polyethylene degradation. Uemichi, Yoshio; Makino, Yutaka; Kanazuka, Takaji, *Degradation of polyethylene to aromatic hydrocarbons over metal-supported activated carbon catalysts*, Journal of Analytical and Applied Pyrolysis (1989), 14(4), 331-44.

See also the following. Tabatabaenian, K.; Mamaghani, M.; Neshat, A.; Masjedi, M. Synthesis and Spectroscopic Studies of New Substituted Dinuclear $\eta^5$-4,5,6,7-Tetrahydroindenyl Ruthenium Complexes. *Russian Journal of Coordination Chemistry.* 2003, 29, 7, 501. Austin, R. N.; Clark, T. J.; Dickson, T. E.; Killian, C. M.; Nile, T. A.; Shabacker, D. J.; McPhail, T. A. Synthesis and Properties of Novel Substituted 4,5,6,7-tetrahydroindenes and Selected Metal Complexes. *Journal of Organometallic Chemistry.* 1995, 491, 11. Conia, J. M.; Leriverend, M. L. Tetrahedron Letters. 1968, 17. 2101 (Conia et al.). L. Rand and R. J. Dolinski, *J. Org. Chem.*, 1966, 31, 3063 and L. Rand and R. J. Dolinski, *J. Org. Chem.*, 1966, 31, 4061 (collectively "Rand and Dolinski"). Yokota, K.; Kohsaka, T.; Ito, K.; Ishihara, N. Consideration of Mechanism of Styrene/Ethylene Copolymerization with Half-Titanocene Catalysts. *Journal of Polymer Science.* 2005, 43, 5041. JP10316694A to Tetsuya, I., et. al. Brancaccio G.; Lettieri, G.; Monforte, P.; Larizza, A. Farmaco, *Edizione Scientifica.* 1983, 9, 702-8. Eaton, P. E.; Carlson, G. R.; Lee, J. T. Phosphorus Pentoxide-Methanesulfonic Acid. A Convenient Alternative to Polyphosphoric Acid. *J.Org. Chem.* 1978, 38, 4071. Paquette, L. A.; Stevens, K. E., Can. *J. Chem.* 1984, 62, 2415. Paquette, L. A.; Cheney, D. L., *J. Org. Chem.* 1989, 54, 3334. *J.Org. Chem.* 1966, 3065.

Conia, et al. reported that reacting cyclohexene and crotonic acid in presence of polyphosphoric acid (PPA) exclusively gave as a sole product 2,3,4,5,6,7-hexahydro-3-methyl-1H-inden-1-one (structure 1 in Conia et al.). Conia et al. reported reacting cyclopentyl crotonate or cyclohexyl crotonate in the presence of PPA gave 3-methyl-bicyclo[3.3.0]-2-octen-1-one (40% yield, Table 1 in Conia et al.) or 2,3,4,5,6,7-hexahydro-3-methyl-1H-inden-1-one (60% yield, Table 2 in Conia et al.), respectively.

Rand and Dolinski use polyphosphoric acid (PPA) or a mixture of phosphorous pentoxide ($P_2O_5$ or $P_4O_{10}$) and PPA to catalyze the reaction of a cycloheptene, cyclohexene, or cyclopentene with an alpha,beta-unsaturated carboxylic acid such as acrylic acid or crotonic acid gives a reaction mixture that contains or is free of an ester by-product such as cycloheptyl crotonate, cyclohexyl crotonate, or cyclopentyl crotonate. Relatively how much of the ester by-product is made is said to depend on the amount of phosphorous pentoxide used in the mixture with PPA or the amount of the PPA or $P_2O_5$/PPA mixture relative to the amount of cycloalkene.

SUMMARY

We discovered an alternative shorter synthesis of an (unsubstituted or substituted)-4,5,6,7-tetrahydroindenyl-metal dichloride complex that does not use a hydrogenation catalyst, a hydrogenation step, or a hydrogenation catalyst filtration step. The inventive (unsubstituted or substituted)-4,5,6,7-tetrahydroindenyl-metal dichloride complex made thereby, and the inventive (unsubstituted or substituted)-4,5,6,7-tetrahydroindenyl-metal dimethyl catalyst made therefrom, and polyolefins made therewith are beneficially free of (added) hydrogenation catalyst metals such as platinum, palladium, nickel, rhodium, and ruthenium. As discussed above, polyolefin degradation problems have been attributed to hydrogenation catalyst metals are reported in the literature, and thus the inventive polyolefin beneficially would inherently avoid any such problem(s). As such, the inventive polyolefin could have longer stability or less degradation than prior polyolefins made with a catalyst synthesized using a hydrogenation step. The instability or degradation could appear over a long period of time as discoloration and/or a change in molecular weight distribution of the polyolefin, or some other manifestation thereof.

The inventive method comprises synthesizing a cyclic organic compound via reaction of an unsubstituted or substituted cyclohexene with an unsubstituted or substituted acrylic acid in the presence of phosphoric and/or sulfonic acid reagent to make the cyclic organic compound. Also, a method of synthesizing a ligand for a transition metal, and a related substituted ligand-metal complex and catalyst, from the unsubstituted or substituted cyclohexene and unsubstituted or substituted acrylic acid. Also, the cyclic organic compound, ligand, and substituted ligand-metal complex and catalyst synthesized thereby. Also a method of polymerizing an olefin with the catalyst to give a polyolefin, and the polyolefin made thereby.

DETAILED DESCRIPTION

The Summary and Abstract are incorporated here by reference.

Certain inventive embodiments are described below as numbered aspects for easy cross-referencing. Additional embodiments are described elsewhere herein.

Aspect 1. A method of synthesizing a bicyclo[4.3.0]nonene compound, the method comprising (A) contacting a compound of formula (1) ("compound (1)"):

(1)

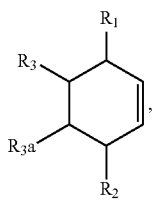

wherein R1, R2, R3, and R3a are independently H or (C$_1$-C$_4$)alkyl, or any two adjacent R1 to R3a groups are bonded together to form a (C$_1$-C$_4$)alkylene and each of the remaining groups of R1 to R3a independently is H or (C$_1$-C$_4$)alkyl, with a compound of formula (2) ("compound (2)"):

(2)

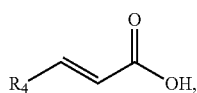

wherein R4 is H or (C$_1$-C$_4$)alkyl, in the presence of an effective amount of a phosphoric and/or sulfonic acid reagent and under reaction conditions sufficient to make a compound of formula (3) ("compound (3)"):

(3)

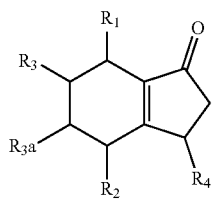

and/or its oxo/R4 regioisomer; wherein R1 to R4 are as defined above; and with the proviso that when each of R1 to R3a is H (i.e., each of R1, R2, R3, and R3a is H) and R4 is methyl, the phosphoric and/or sulfonic acid reagent and contacting step (A) are free of a polyphosphoric acid (PPA). In some aspects, the phosphoric and/or sulfonic acid reagent and contacting step (A) are free of PPA. The "/" in "oxo/R4 regioisomer" indicates the groups that are in different positions in the oxo/R4 regioisomer relative to the compound (3). That is, the positions of the oxo (=O) and R4 substituents are switched with each other relative to their positions in the compound (3). Thus, in the oxo/R4 regioisomer the oxo is bonded to the carbon atom bearing R4 in compound (3) and the R4 in the oxo/R4 regioisomer is bonded to the carbon atom bearing the oxo in compound (3). The regioisomer relationships are illustrated by the compounds of formulas (3a) and (3b):

(3a)

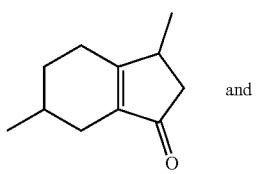

and (3b)

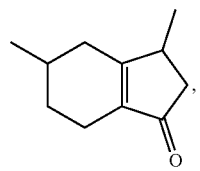

which are methyl/oxo regioisomers wherein compound (3a) is a compound of formula (3) wherein R1, R2, and R3a are H and R3 and R4 are methyl and compound (3b) is a compound of formula (3) wherein R1, R2, and R3 are H and R3a and R4 are methyl. Functional groups that are in different positions in other regioisomers described below may be designated using "group/group" (e.g., R5/R4) in a similar manner.

Aspect 2. A method of synthesizing a ligand for a transition metal, the method comprising: (A) synthesizing the compound (3):

(3)

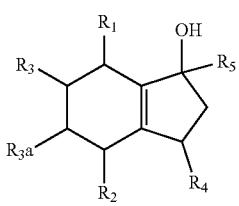

and/or its oxo/R4 regioisomer, according to step (A) of aspect 1, wherein R1 to R4 are as defined above (in aspect 1); (B) contacting the compound (3) and/or its oxo/R4 regioisomer with either a hydride-functional reducing agent or a (C$_1$-C$_4$)alkyl lithium, under reaction conditions sufficient to make a compound of formula (4) ("compound (4)"):

(4)

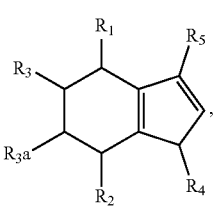

and/or its (HO,R5)/R4 regioisomer, respectively, wherein R1 to R4 are as defined above and R5 is either H or (C$_1$-C$_4$)alkyl, respectively; and (C) contacting the compound (4) and/or its (HO,R5)/R4 regioisomer with dehydration reaction conditions to make a compound of formula (5) ("compound (5)"):

(5)

and/or its R5/R4 regioisomer, respectively; wherein R1 to R5 are as defined above. The "/" identifies the groups that are in different positions in the respective regioisomers relative to compound (4) or (5). In some aspects the method further comprises a separation step between steps (A) and (B), the separation step comprising separating the compound (3) from its oxo/R4 regioisomer to give a purified compound (3) and/or a purified oxo/R4 regioisomer. Alternatively, in some aspects the method further comprises a separation step between steps (B) and (C), the separation step comprising separating the compound (4) from its (HO,R5)/R4 regioisomer to give a purified compound (4) and/or a purified (HO,R5)/R4 regioisomer. Alternatively, in some aspects the method further comprises a separation step after step (C), the separation step comprising separating the compound (5) from its R5/R4 regioisomer to give a purified compound (5) and/or a purified R5/R4 regioisomer. Method steps downstream from one of the separation steps may be free of either the separated compound or its regioisomer, as the case may be and ultimately make the compound (5) that is free of its R5/R4 regioisomer or make the R5/R4 regioisomer that is free of the compound (5). The separation steps may comprise fractional distillation, fractional crystallization, or chromatography such as gas chromatography or liquid chromatography. E.g., room pressure, medium pressure or high pressure liquid chromatography on a silica gel column using one or more organic solvents as eluent.

Aspect 3. A method of synthesizing a zirconocene dichloride complex, the method comprising synthesizing the compound (5) and/or its R5/R4 regioisomer according to steps (A) to (C) of aspect 2; (D) contacting the compound (5) and/or its R5/R4 regioisomer with an alkyl lithium under reaction conditions sufficient to make a compound of formula (6) ("compound (6)"):

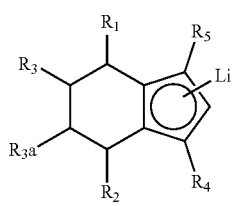

(6)

and/or its R5/R4 regioisomer; and (E) contacting the compound (6) and/or its R5/R4 regioisomer with a compound of formula (7) ("compound (7)"):

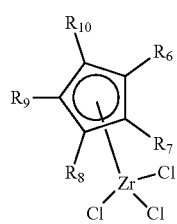

(7)

under reaction conditions sufficient to make a compound of formula (8) ("compound (8)"):

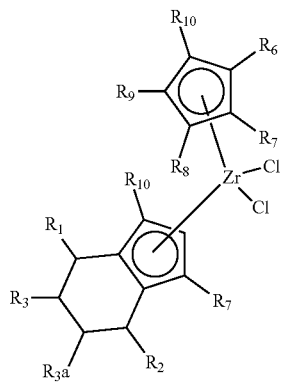

(8)

and/or its R5/R4 regioisomer, wherein R1 to R5 are as defined above (in aspect 2) and each of R6 to R10 is independently H or $(C_1-C_4)$alkyl. Method steps downstream from one of the separation steps described previously may be free of either the separated compound or its regioisomer, as the case may be and ultimately make the compound (8) that is free of its R5/R4 regioisomer or make the R5/R4 regioisomer that is free of the compound (8). The compound (7) may be made by contacting a R6 to R10-functional cyclopentadiene with an alkyl lithium under reaction conditions sufficient to make a R6 to R10-functional cyclopentadienyl lithium, and contacting the R6 to R10-functional cyclopentadienyl lithium with zirconium tetrachloride under reaction conditions sufficient to make the compound (7). The R6 to R10-functional cyclopentadiene may be synthesized by known methods or obtained from a commercial source.

Aspect 4. A method of synthesizing a zirconocene dimethyl complex, the method comprising synthesizing the compound (8) and/or its R5/R4 regioisomer according to steps (A) to (E) of aspect 3; and (F) contacting the compound (8) and/or its R5/R4 regioisomer with an effective amount of methyl magnesium bromide under reaction conditions sufficient to make a compound of formula (9) ("compound (9)"):

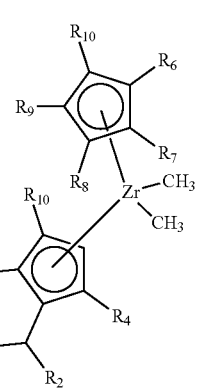

(9)

and/or its R5/R4 regioisomer, wherein R1 to R10 are as defined above (in aspect 3). Method steps downstream from one of the separation steps described previously may be free of either the separated compound or its regioisomer, as the case may be and ultimately make the compound (9) that is free of its R5/R4 regioisomer or make the R5/R4 regioisomer that is free of the compound (9).

Aspect 5. The method of any one of aspects 1 to 4, wherein the phosphoric and/or sulfonic acid reagent is a polyphosphoric acid (PPA); a mixture of a phosphorous pentoxide and methanesulfonic acid ("$P_2O_5/H_3CSO_3H$ mixture"), or a reaction product thereof; or a combination of a PPA and a $P_2O_5/H_3CSO_3H$ mixture, or a reaction product of thereof; with the proviso that when each of R1 to R3a is H and R4 is methyl, the phosphoric and/or sulfonic acid reagent and the contacting step (A) are free of the PPA.

Aspect 6. The method of any one of aspects 1 to 5 wherein the phosphoric and/or sulfonic acid reagent is a polyphosphoric acid (PPA); with the proviso that at least one of R1 to R3a is ($C_1$-$C_4$)alkyl or R4 is H. Alternatively, R1 to R3a is ($C_1$-$C_4$)alkyl and R4 is H.

Aspect 7. The method of any one of aspects 1 to 5, wherein the phosphoric and/or sulfonic acid reagent is, or consists essentially of, the $P_2O_5/H_3CSO_3H$ mixture, or a reaction product thereof. The "consists essentially of" means the reagent, and the reaction, is free of a PPA. In some aspects the $P_2O_5/H_3CSO_3H$ mixture is a 0.1/1 (weight/weight) $P_2O_5/H_3CSO_3H$ mixture, known as Eaton's reagent.

Aspect 8. The method of any one of aspects 1 to 5, wherein the phosphoric and/or sulfonic acid reagent is the combination of the PPA and the $P_2O_5/H_3CSO_3H$ mixture, or a reaction product thereof. In some aspects the $P_2O_5/H_3CSO_3H$ mixture is a 0.1/1 (weight/weight) $P_2O_5/H_3CSO_3H$ mixture, known as Eaton's reagent.

Aspect 9. The method of any one of aspects 1 to 8, characterized by any one of limitations (i) to (ix): (i) wherein at least one of R1 to R3a is a ($C_1$-$C_4$)alkyl or R4 is H; (ii) wherein each of R1 to R4 is H; (iii) wherein each of R1 to R3a is H and R4 is methyl; (iv) wherein in compound (1) each of R1, R2, and R3a is H and R3 is methyl; in compound (2) R4 is methyl; and in compound (3) each of R1, R2, and R3a is H and each of R3 and R4 is methyl; and in its oxo/R4 regioisomer each of R1, R2, and R3 is H and each of R3a and R4 is each methyl; (v) wherein R1 and/or R2 is methyl and R3 and R3a is H; (vi) wherein R1 is methyl, R2 is 1-methylethyl (i.e., isopropyl), and R3 and R3a are H; (vii) wherein R1 is 1-methylethyl (i.e., isopropyl), R2 is methyl, and R3 and R3a are H; (viii) wherein R1 and R2 independently are ($C_1$-$C_4$)alkyl, R3 and R3a are H, and the stereochemistry of the carbon atom bonded to R1 is (R) and the stereochemistry to the carbon atom bonded to R2 is (S); and (ix) wherein R1 and R2 independently are ($C_1$-$C_4$)alkyl, R3 and R3a are H, and the stereochemistry of the carbon atom bonded to R1 is (S) and the stereochemistry to the carbon atom bonded to R2 is (R). Alternatively any one of limitations (x) to (xxi): (x) both (vi) and (viii); (xi) both (vi) and (ix); (xii) both (vii) and (viii); (xiii) both (vii) and (ix); (xiv) wherein R5 is H; (xv) wherein R5 is methyl; (xvi) both (i) and (xiv) or (xv); (xvii) both (ii) and (xiv) or (xv); (xviii) both (iii) and (xiv) or (xv); (xix) both (iv) and (xiv) or (xv); (xx) both (v) and (xiv) or (xv); and (xxi) any two adjacent R1 to R3a groups are bonded together to form a ($C_1$-$C_4$) alkylene and the remaining group of R1 to R3a is H or ($C_1$-$C_4$)alkyl.

Aspect 10. The compound (3) or its oxo/R4 regioisomer made by the method of aspect 1, the compound (4) or its (HO,R5)/R4 regioisomer made by the method of aspect 2, the compound (5) or its R5/R4 regioisomer made by the method of aspect 2, the compound (6) or (8), or their respective R5/R4 regioisomers made by the method of aspect 3, or the compound (9) or its R5/R4 regioisomer made by the method of aspect 4; wherein the compound or its regioisomer is free of platinum, palladium, nickel, rhodium, and ruthenium. The term "free of" means contains no detectable presence of. In some aspects the compound is any one of compounds (8-1) and (8-2) described later in the Examples; alternatively any one of compounds (9-1) and (9-2) described later in the Examples.

Aspect 11. A method of polymerizing an olefin, the method comprising contacting ethylene and/or an alpha-olefin with a catalyst made by contacting the compound (8) or (9), or its R5/R4 regioisomer, made by the method of aspect 4, with an activator, under conditions sufficient to make a polyolefin polymer comprising a polyethylene homopolymer, an ethylene/alpha-olefin copolymer, or a poly(alpha-olefin) homopolymer. In some aspects the catalyst is made from compound (8); alternatively from any one of compounds (8-1) and (8-2) described later in the Examples; alternatively from compound (9); alternatively from compound (9-1) and (9-2); described later in the Examples.

Aspect 12. The polyolefin polymer made by the method of aspect 11 and being free of platinum, palladium, nickel, rhodium, and ruthenium. In some aspects the polyolefin polymer is characterized by a butyl branch frequency (BBF) of 0.5 to less than 1.0, alternatively 0.6 to less than 1.0, measured according to the Butyl Branch Frequency (BBF) Test Method, described later.

Another embodiment is any one of the foregoing aspects wherein 3,3-dimethyl-1-cyclohexene is used in place of the compound (1). The 3,3-dimethyl-1-cyclohexene is a geminal-dimethyl analog of cyclohexene and is a derivative of compound (1) wherein R2, R3 and R3a are H, R1 is methyl, and the carbon atom bearing R1 is substituted with a second methyl. The embodiments yield analogs of compounds (3) to (6), (8) and (9) wherein R2, R3 and R3a are H, R1 is methyl, and the carbon atom bearing R1 is substituted with a second methyl.

Compound: a molecule or a collection of same molecules.

Contacting: physically touching. In synthesizing context, contacting may be facilitated by a solvent that dissolves the compounds or materials being contacted.

Copolymer: macromolecular compound containing, in the same molecular entity or molecule, constitutional units derived from polymerizing a monomer and units derived from polymerizing at least one different monomer (comonomer).

Free of a polyphosphoric acid: no added polyphosphoric acid (PPA), alternatively no added, or in situ generated, PPA.

Homopolymer: macromolecular compound containing, in the same molecular entity or molecule, constitutional units, each of which is derived from polymerizing the same monomer.

Independently: without regard to or dependence on another.

Mixture: intimate blend of two or more compounds or materials.

Oxo: =O. E.g., as bonded to carbon atom in a carbonyl group (C=O).

Reaction product: different molecular entity than that from which it is made via a chemical reaction. The difference may be oxidation state and/or covalent bond(s).

Reagent, in the context of a reaction (e.g., step (A)): compound or mixture added to a reaction system to cause or enhance a desired chemical reaction.

Regioisomer: a positional isomer without any differences in bond multiplicities.

"$R_\#$" and "R #", wherein # means number, mean the same. E.g., $R_1$ and R1 are the same and mean a first R group; $R_2$ and R2 are the same and mean a second R group; and so on.

Step, in the context of the method of synthesizing: distinct chemical reaction, often with distinct reaction conditions and/or physical manipulations.

Stereochemistry: isomerism due to differences in spatial arrangement of atoms without any differences in connectivity or bond multiplicities between isomers.

Synthesizing: purposeful execution of one or more distinct chemical reactions or steps to manufacture a reaction product.

Zirconocene: complex comprising a zirconium atom bonded to one or two unsubstituted or substituted cyclopentadienyl-type groups, and optionally other ligands (e.g., $CH_3$, Cl).

Activator (for activating compound (9) and/or its R5/R4 regioisomer to form a catalyst). Also known as co-catalyst. Any metal containing compound, material or combination of compounds and/or substances, whether unsupported or supported on a support material, that can activate compound (9) and/or its R5/R4 regioisomer to give a catalyst and an activator species. The activating may comprise, for example, abstracting at least one leaving group (e.g., at least one methyl) from the Zr of compound (9) or its R5/R4 regioisomer to give the catalyst. The activator may be a Lewis acid, a non-coordinating ionic activator, or an ionizing activator, or a Lewis base, an alkylaluminum, or an alkylaluminoxane. The alkylaluminum may be a trialkylaluminum, alkylaluminum halide, or alkylaluminum alkoxide (diethylaluminum ethoxide). The trialkylaluminum may be trimethylaluminum, triethylaluminum ("TEAl"), tripropylaluminum, triisobutylaluminum, and the like. The alkylaluminum halide may be diethylaluminum chloride. The alkylaluminoxane may be a methyl aluminoxane (MAO), ethyl aluminoxane, or isobutylaluminoxane. The activator may be a MAO that is a modified methylaluminoxane (MMAO). The corresponding activator species may be a derivative of the Lewis acid, non-coordinating ionic activator, ionizing activator, Lewis base, alkylaluminum, or alkylaluminoxane, respectively. The activator species may have a different structure or composition than the activator from which it is derived and may be a by-product of the activation reaction. The metal of the activator typically is different than zirconium. The molar ratio of metal content of the activator to zirconium content of compound (9) and/or its R5/R4 regioisomer may be from 1000:1 to 0.5:1, alternatively 300:1 to 1:1, alternatively 150:1 to 1:1.

Alkyl means an unsubstituted univalent saturated acyclic hydrocarbon that is straight chain (1 or more carbon atoms), branched chain (if 3 or more carbon atoms), or cyclic (if 3 or more carbon atoms). Each $(C_1-C_4)$alkyl is independently methyl, ethyl, propyl, 1-methylethyl, butyl, 1-methylpropyl, 2-methylpropyl, or 1,1-dimethylethyl. Alternatively each $(C_1-C_4)$alkyl is independently a $(C_1-C_3)$alkyl; alternatively a $(C_2-C_4)$alkyl; alternatively $(C_1-C_2)$alkyl; alternatively $(C_2-C_3)$alkyl; alternatively $(C_3-C_4)$alkyl; alternatively methyl or $(C_3)$alkyl. In some aspects each $(C_1-C_4)$alkyl is independently a $(C_1-C_3)$alkyl and each $(C_1-C_3)$alkyl is independently methyl, ethyl, propyl, or 1-methylethyl; alternatively methyl, propyl, or 1-methylethyl; alternatively methyl; alternatively ethyl; alternatively propyl; alternatively 1-methylethyl. Substituted alkyl is an alkyl as defined above except wherein one or more hydrogen atoms is formally replaced by a substituent such as unsubstituted alkyl, halogen, or alkylcarboxylic ester.

Alkyl lithium is a compound of formula alkyl-Li. Examples of alkyl lithium are methyl lithium, ethyl lithium, propyl lithium, n-butyl lithium, sec-butyl lithium, t-butyl lithium, and pentyl lithium. The $(C_1-C_4)$alkyl lithium is an alkyl lithium wherein the alkyl is methyl, ethyl, propyl, 1-methyl ethyl, butyl, 1-methylpropyl, 2-methylpropyl (sec-butyl), or 1,1-dimethylethyl (t-butyl).

Alkylene is unsubstituted divalent saturated acyclic hydrocarbon that is straight chain (1 or more carbon atoms), branched chain (if 3 or more carbon atoms), or cyclic (if 3 or more carbon atoms). Each $(C_1-C_4)$alkylene is independently methylene ($CH_2$), ethylene ($CH_2CH_2$), propylene ($CH_2CH_2CH_2$), 1-methylethylene ($CH(CH_3)CH_2$), butylene (($CH_2)_4$), 1-methylpropylene ($CH(CH_3)CH_2CH_2$), 2-methylpropylene ($CH_2CH(CH_3)CH_2$), or 1,1-dimethylethylene ($C(CH_3)_2CH_2$. Substituted alkylene is an alkylene as defined above except wherein one or more hydrogen atoms is formally replaced by a substituent such as unsubstituted alkyl, halogen, or alkylcarboxylic ester.

Bicyclo[4.3.0]nonene compounds are molecules having a six-membered carbocyclic ring fused to a five-membered carbocyclic ring. The five-membered carbocyclic ring may contain a carbon-carbon double bond, which may be shared at the fusion point with the six-membered carbocyclic ring. Examples are (3), its oxo/R4 regioisomer, (3a), (3b), (4), its (HO,R5)/R4 regioisomer, (5), its R5/R4 regioisomer, (6), its R5/R4 regioisomer, (8), its R5/R4 regioisomer, (9), and its R5/R4 regioisomer.

Combination of polyphosphoric acid (PPA) and a mixture of a phosphorous pentoxide and methanesulfonic acid ("$P_2O_5/H_3CSO_3H$ mixture") is a physical blend of PPA and a preformed $P_2O_5/H_3CSO_3H$ mixture or a physical blend of PPA, $P_2O_5$, and $H_3CSO_3H$. In some aspects the method further comprises limitation (i) or (ii): (i) a step of preforming the combination of PPA and $P_2O_5/H_3CSO_3H$ mixture before the contacting step (A) and in the absence of at least one, alternatively each of the compounds (1) to (3) and the oxo/R4 regioisomer; or (ii) wherein the contacting step (A) further comprises contacting PPA and the $P_2O_5/H_3CSO_3H$ mixture together in the presence of at least one, alternatively each of the compounds (1) and (2) to form the combination of PPA and $P_2O_5/H_3CSO_3H$ mixture in situ.

Compound means a molecule or collection of molecules. When R1 to R3a is H, compound (1) is cyclohexene. When at least one of R1 to R3a is $(C_1-C_4)$alkyl, compound (1) is a substituted cyclohexene. When R4 is H, the compound (2) has CAS number 79-10-7 and is known as acrylic acid. When R4 is methyl, the compound (2) has CAS number 107-93-7 and is known as (E)-2-butenoic acid, crotonic acid, or (trans) 3-methylacrylic acid. Compounds (1) and (2) are widely available from commercial suppliers.

Dehydration reaction conditions include temperature and reagents effective for enhancing rate of loss of water from compound (4) and/or its (HO,R5)/R4 regioisomer. Example of such reagents are 1 Molar (M) or higher hydrochloric acid (aqueous HCl) or anhydrous HCl or Amberlyst 15 solid acid catalyst in an organic solvent such as diethyl ether, ethanol, tetrahydrofuran or toluene. The hydrochloric acid may be from 1 M to 8 M, alternatively from 2 M to 6 M.

Effective amount is a quantity sufficient for enabling the making of a detectable amount of intended product. An effective amount of the phosphoric and/or sulfonic acid reagent is a quantity thereof sufficient for enabling the making of a detectable amount of compound (3) and/or its oxo/R4 regioisomer. Detectable amounts may be detected, and optionally characterized, by any suitable analytical method such as 1H-nuclear magnetic resonance (1H-NMR), high performance liquid chromatography (HPLC, versus a known standard), gas chromatography (GC, versus a known standard), or mass spectrometry; typically 1H-NMR. The effective amount of the phosphoric and/or sulfonic acid reagent used in step (A) may vary depending upon its composition, reaction conditions, and costs. A skilled person may determine an optimal effective amount thereof by starting with an initial reaction mixture of (1), (2), and 95 wt % of the phosphoric and/or sulfonic acid reagent, and thereafter systematically try reaction mixtures containing lower wt % of the phosphoric and/or sulfonic acid reagent until an optimal result under the reaction conditions is found. When the phosphoric and/or sulfonic acid reagent is PPA, the $P_2O_5/H_3CSO_3H$ mixture, or the combination of PPA and $P_2O_5/H_3CSO_3H$ mixture, the effective amount may be from 50 to 95 wt %, alternatively from 50 to 80 wt % based on total weight of (1), (2), and the phosphoric and/or sulfonic acid reagent. Alternatively, the effective amount of the $P_2O_5/H_3CSO_3H$ mixture may be from 1 to 10 mole equivalents (mol equiv.), alternatively 1 to 5 mol equiv., alternatively 1 to 3 mol equiv. relative to the number of moles of compound (1). E.g., if 1.0 mole of compound (1) is used in the contacting step (A), then the effective amount of the $P_2O_5/H_3CSO_3H$ mixture may be from 1 to 10 moles, alternatively 1 to 5 moles, alternatively 1 to 3 moles.

Hydride-functional reducing agent means a compound having a metal-H bond capable of adding to an oxo group of a ketone to give a tertiary alcohol. Suitable metals include Al and B. Suitable hydride-functional reducing agents are lithium aluminum hydride ($LiAlH_4$), diisobutyl aluminum hydride (i-$Bu_2AlH$), and sodium borohydride ($NaBH_4$).

Methanesulfonic acid is a compound of formula $H_3CSO_3H$ and has CAS number 75-75-2 and is widely available from commercial suppliers.

Mixture of a phosphorous pentoxide and methanesulfonic acid or $P_2O_5/H_3CSO_3H$ mixture is a blend or reaction product of phosphorous pentoxide and methane sulfonic acid. The weight/weight ratio of $P_2O_5/H_3CSO_3H$ in the mixture may be from 0.1 to 1 alternatively 0.15 to 1, alternatively 0.2 to 1. The 0.1/1 (wt/wt) $P_2O_5/H_3CSO_3H$ mixture is commercially available and may be referred to as Eaton's reagent. The mixture of $P_2O_5$ and $CH_3SO_3H$ may be formed in situ in the presence of the compound (1) and/or (2), such as prior to or during the contacting step (A). Alternatively, the mixture of $P_2O_5$ and $CH_3SO_3H$ may be preformed before contacting step (A). It is convenient to preform the $P_2O_5/CH_3SO_3H$ mixture before contacting step (A), and store the resulting preformed mixture for later use in embodiments of the contacting step (A). In some aspects the method further comprises limitation (i) or (ii): (i) a step of preforming the $P_2O_5/H_3CSO_3H$ mixture before the contacting step (A) and in the absence of at least one, alternatively each of the compounds (1) and (2); or (ii) wherein the contacting step further comprises contacting a phosphorous pentoxide and methanesulfonic acid together in the presence of at least one, alternatively each of the compounds (1) and (2) to form the $P_2O_5/H_3CSO_3H$ mixture in situ.

Phosphoric and/or sulfonic acid reagent is an acidic material having O—P(O)—OH acid groups and/or C—S(O)$_2$—OH acid groups, or an acidic reaction product thereof. The phosphoric and/or sulfonic acid reagent may be, or may consist essentially of, a mixture of a phosphorous pentoxide and methanesulfonic acid ("$P_2O_5/H_3CSO_3H$ mixture"), or a reaction product thereof; alternatively a polyphosphoric acid (PPA); alternatively a combination of a $P_2O_5/H_3CSO_3H$ mixture and a PPA, or a reaction product thereof.

Polyphosphoric acid or PPA has CAS no. 8017-16-1 and is a compound generally of formula HO—[P(=O)(OH)]$_n$—H, wherein subscript n indicates degree of polymerization. PPAs are widely available from commercial suppliers.

Phosphorous pentoxide is a compound of formula $P_2O_5$ and has CAS number 1314-56-3 and is widely available from commercial suppliers.

In some aspects each reactant, reagent, solvent, or other material used in the inventive methods, and each product thereof, is free of Pt, Ni, Pd, Rh, and Ru.

The "reaction conditions sufficient to make" mean appropriate for the desired chemical transformation, as is well understood in the art, and include reaction temperature; reaction pressure; reaction atmosphere; reaction solvent, if any; reactant and reagent concentrations; molar ratios of reactants to each other and to reagents; and absence of negating compounds. Reaction pressure is typically room pressure (e.g., 101 kilopascals (kPa), except higher for olefin polymerization reactions. If desired reactions (e.g., steps (A) to (F)) may be carried out in a fume hood under an anhydrous molecular nitrogen gas atmosphere or using Schlenck line techniques and conditions.

Reaction temperatures under reaction conditions sufficient to make may vary from step to step. For example, in step (A) (cyclocondensation) when the phosphoric and/or sulfonic acid reagent is PPA, the under reaction conditions sufficient to make compound (3) and/or its oxo/R4 regioisomer may include a reaction temperature of at least 40° C., alternatively at least 50° C., alternatively at least 65° C.; and at most 100° C., alternatively at most 95° C., alternatively at most 90° C., alternatively at most 80° C. In step (A) when using the $P_2O_5/H_3CSO_3H$ mixture the reaction temperature may be from −78° to 30° C., alternatively from −30° to 25° C., alternatively from 0° to 25° C. In steps (B) (hydride reduction or alkyl lithium addition), (D) (deprotonation of a cyclopentadiene), (E) (forming a zirconocene dichloride) and (F) (forming a zirconocene dimethyl) the reaction temperatures may be independently from −30° to 110° C., alternatively from 0° to 50° C., alternatively from 10° to 30° C. In step (C) (dehydration) the reaction temperature may be from 0° to 120° C., alternatively from 20° to 110° C., alternatively from 30° to 100° C.

The use or not of solvent and the type of solvent if used under reaction conditions sufficient to make may vary from step to step. Step (A) may be free of solvent or may employ a solvent. When the phosphoric and/or sulfonic acid reagent is PPA, a solvent may be omitted. When the phosphoric and/or sulfonic acid reagent is the $P_2O_5/H_3CSO_3H$ mixture, a polar aprotic solvent may be employed. The polar aprotic solvent may be selected from sulfolane, 1,2-dimethoxyethane, 1-methoxy-2-(2-methoxyethoxy)ethane, and mixtures of any two or more thereof. The amount of polar aprotic solvent employed is not particularly important. The foregoing polar aprotic solvents may serve to solubilize the compounds (1) and (2) and/or the $P_2O_5/H_3CSO_3H$ mixture. The amount of solvent employed may be sufficient to prepare a starting solution of that is from 0.5 Molar (M) to 5 M, or 1 M to 2.5 M of $P_2O_5/H_3CSO_3H$ mixture in the compound (2). The polar aprotic solvent may allow the contacting step (A) to be performed at lower temperatures within the ranges given above therefor. A polar aprotic solvent is used for the $P_2O_5/H_3CSO_3H$ mixture because a protic solvent is expected to undesirably react with the $P_2O_5/H_3CSO_3H$ mixture, which is a powerful dehydrating agent. The polar aprotic solvent may be of intermediate polarity in order to co-solubilize the compounds (1) and (2) and $P_2O_5/H_3CSO_3H$ mixture. The polar aprotic solvent may be capable of producing a homogeneous solution of the compounds (1) and (2) at 25° C., alternatively at 10° C., alternatively at 0° C. A homogeneous solution is not required for successful reaction of compounds (1) and (2) in the presence of the phosphoric and/or sulfonic acid reagent. In steps (B) (hydride reduction or alkyl lithium addition), (D) (deprotonation of a cyclopentadiene), (E) (forming a zirconocene dichloride) and (F) (forming a zirconocene dimethyl) an anhydrous, non-polar aprotic solvent such as an alkyl ether such as diethyl ether, tetrahydrofuran, or dioxane may be used. In step (B) when the hydride-functional reducing agent is used and is lithium aluminum hydride or diisobutyl aluminum hydride, the anhydrous, non-polar solvent is used. In step (B) when the hydride-functional reducing agent is used and is sodium borohydride, a polar protic solvent may be used such as methanol, ethanol, 2-propanol, or 1-methoxy-2-(2-methoxyethoxy)ethane. The alkyl lithium reagent may be dissolved in anhydrous alkane solvent such as hexanes, hexane, or heptane. Grignard reagents such as methyl magnesium bromide may be dissolved in an alkyl ether such as dialkyl ether.

Reaction atmosphere included under reaction conditions sufficient to make may be anhydrous molecular nitrogen gas or Schlenck line conditions for step (A) (cyclocondensation) and air for step (C) (dehydrating). Reaction atmosphere for step (B) (hydride reduction or alkyl lithium addition), (D) (deprotonation of a cyclopentadiene), (E) (forming a zirconocene dichloride) and (F) (forming a zirconocene dimethyl) may be an inert gas such as anhydrous nitrogen, argon or helium gas, or a mixture of any two or more thereof.

Reaction concentrations of reactants and reagents included under reaction conditions sufficient to make may be independently in the range from 0.1 to 1.4 M, alternatively 0.25 to 1 Molar (M), alternatively 0.4 to 1 M.

Molar ratios of reactants to each other and to reagents included under reaction conditions sufficient to make may vary from 0.25 times to 1.5 times theoretical reaction stoichiometry, alternatively from 0.99 times to 1.2 times theoretical reaction stoichiometry, alternatively from 1.0 to 1.1 times theoretical reaction stoichiometry, depending upon the reactants and reagents used. In step (A) (cyclocondensation) the theoretical reaction stoichiometry of compound (1) to compound (2) is 1.0 to 1.0. In step (B) (hydride reduction or alkyl lithium addition), the theoretical reaction stoichiometry of the hydride-functional reducing agent to compound (3) (or its regioisomer) is 0.25 LiAlH4 or NaBH4 to 1.0 compound (3) and 0.5 i-Bu2AlH to 1.0 compound (3) and 1.0 ($C_1$-$C_4$)alkyl lithium to 1.0 compound (3) (or its regioisomer). The theoretical reaction stoichiometry for step (C) (dehydration) is catalytic in acid catalyst up to, typically, 1:1. The theoretical reaction stoichiometry for each of steps (D) (deprotonation of a cyclopentadiene), or (E) (forming a zirconocene dichloride) is typically 1:1. The theoretical reaction stoichiometry for step (F) (forming a zirconocene dimethyl) is 2.0 methyl magnesium bromide to 1.0 compound (8) (or its R5/R4 regioisomer).

Negating agents should not be included under reaction conditions sufficient to make. In step (A) (cyclocondensation), a negating agent may be a quantify of a basic compound that would neutralize the acidity of the phosphoric and/or sulfonic acid reagent or otherwise render it ineffective; or a negating agent may be an unsaturated aliphatic compound that would react with compound (2) before compound (2) could react with compound (1). In steps (B) (hydride reduction or alkyl lithium addition), (D) (deprotonation of a cyclopentadiene), (E) (forming a zirconocene dichloride) and (F) (forming a zirconocene dimethyl), a negating agent would be a protic compound (e.g., a NH functional, OH functional, and/or SH functional compound) or an oxidizing agent. Examples of NH functional compounds are primary and secondary amines and amides. Examples of OH functional compounds are alcohols, carboxylic acids, and oximes. Examples of SH functional compounds are thiols (mercaptans). Examples of NH and OH functional compounds are primary and secondary amino alcohols and amino acids. In step (C) (dehydrating), a negating agent would be added water (not counting water formed as a by-product of the dehydrating step) or a quantity of a basic compound that would neutralize an acid dehydration catalyst used therein.

A compound includes all its isotopes and natural abundance and isotopically-enriched forms. The enriched forms may have medical or anti-counterfeiting uses.

In some aspects any compound, composition, formulation, mixture, or reaction product herein may be free of any one of the chemical elements selected from the group consisting of: H, Li, Be, B, C, N, O, F, Na, Mg, Al, Si, P, S, Cl, K, Ca, Sc, Ti, V, Cr, Mn, Fe, Co, Ni, Cu, Zn, Ga, Ge, As, Se, Br, Rb, Sr, Y, Zr, Nb, Mo, Tc, Ru, Rh, Pd, Ag, Cd, In, Sn, Sb, Te, I, Cs, Ba, Hf, Ta, W, Re, Os, Ir, Pt, Au, Hg, Tl, Pb, Bi, lanthanoids, and actinoids; with the proviso that chemical elements required by the compound, composition, formulation, mixture, or reaction product (e.g., C and H required by a polyolefin or C, H, and O required by an alcohol) are not excluded.

The following apply unless indicated otherwise. Alternatively precedes a distinct embodiment. ASTM means the standards organization, ASTM International, West Conshohocken, Pa., USA. Any comparative example is used for illustration purposes only and shall not be prior art. Free of or lacks means a complete absence of; alternatively not detectable. May confers a permitted choice, not an imperative. Operative means functionally capable or effective. Optional(ly) means is absent (excluded), alternatively is present (included). Properties are measured using a standard test method and conditions for the measuring (e.g., viscosity: 23° C. and 101.3 kPa). Ranges include endpoints, subranges, and whole and/or fractional values subsumed therein, except a range of integers does not include fractional values. Room temperature: 23° C.±1° C. Substituted when referring to a compound means having, in place of hydrogen, one or more substituents, up to and including per substitution.

EXAMPLES

Unless noted otherwise herein, use the following preparations for characterizations. Carry out syntheses under an atmosphere of dry nitrogen in a glovebox when indicated. Perform reactions requiring anhydrous conditions under an atmosphere of dry nitrogen in oven-dried glassware cooled under a stream of dry nitrogen. Anhydrous toluene, hexanes, tetrahydrofuran, diethyl ether and 1,2-dimethoxyethane are from Sigma-Aldrich. Solvents that are used for experiments performed in a nitrogen-filled glovebox are further dried by storage over activated 4 Angstrom (Å) molecular sieves. Cyclopentadienylzirconium (IV) chloride (compound (7) wherein R6-R10 is H, "(Cp)ZrCl$_3$") is purchased from Boulder Scientific and is used as received. Methylcyclopentadienylzirconium (IV) chloride (compound (7) wherein R6-R9 is H and R10 is methyl, "(MeCp)ZrCl$_3$") is purchased as a complex with dimethoxyethane (DME) from Boulder Scientific and is used as received. All other reagents are purchased from Sigma-Aldrich and are used as received. For example, 0.1/1 (wt/wt) P2O5/MeSO3H mixture may be purchased from Sigma-Aldrich CAS #39394-84-8.

$^1$H-NMR (proton nuclear magnetic resonance spectroscopy) chemical shift data are reported in parts per million (ppm) down field relative to tetramethylsilane (TMS), δ scale, using residual protons in deuterated solvent as references. The $^1$H-NMR chemical shift data measured in CDCl$_3$ are referenced to 7.26 ppm, data measured in benzene-d6 (C$_6$D$_6$) to 7.16 ppm, data measured in tetrahydrofuran-d8 (THF-d8) to 3.58 ppm. $^1$H-NMR chemical shift data are reported in the format: chemical shift in ppm (multiplicity, coupling constant(s) in Hertz (Hz), and integration value. Multiplicities are abbreviated s (singlet), d (doublet), t (triplet), q (quartet), pent (pentet), m (multiplet), and br (broad).

Butyl Branch Frequency (BBF) Test Method: Butyl Branching Frequency is number of butyl branches per 1000 main chain carbon atoms of a poly(ethylene-co-1-hexene) copolymer. To prepare test sample, add approximately 2.74 g of a 50/50 mixture of tetrachloroethane-d$_2$/orthodichlorobenzene containing 0.025 M Cr(AcAc)$_3$ to 0.15 g of test sample of the copolymer in a 10 mm NMR tube (Norell 1001-7). Remove oxygen manually by purging tube with nitrogen using a Pasteur pipette for 1 minute. Dissolve and homogenize test sample by heating the tube and its contents to 150° C. in a heating block. Visually inspect heated test sample to ensure homogeneity (thorough mixing). Without allowing heated test sample to cool, insert it into a heated (120° C.) NMR probe. Allow inserted sample to thermally equilibrate at the probe temperature for seven minutes. Then acquire NMR data using a Bruker 400 MHz spectrometer, equipped with a Bruker CryoProbe using 320 transient scans, and a six second pulse repetition delay. Make all measurements on a non-spinning sample in locked mode. Internally reference $^{13}$C NMR chemical shifts to the EEE triad at 30 ppm. Determine short chain branches (SCB) derived from 1-hexene (C4 branches) comonomeric units by setting the integral value for the entire spectrum (from ~40 to 10 ppm) to 1,000, and then calculate BBF according to the following formula: BBF=(a+b/2+c+d/2+e)/5, wherein a, b, c, d, e and f are the integrated regions of the $^{13}$C NMR signals at 38.2, 34.6, 34.2, 27.3 and 23.4 ppm, respectively.

GC/MS (EI) means gas chromatography-mass spectrometry (electron ionization).

Inventive Example 1: synthesis of compound (3-1) using PPA: compound (3) wherein R1 to R3a is H and R4 is methyl. Charge a 3-necked, 250 mL round bottom flask fitted with a mechanical stirrer and under a nitrogen atmosphere with polyphosphoric acid (PPA) (155 g), and warm up flask contents to 80° C. until the PPA becomes soluble. Add (E)-2-butenoic acid (compound (2) wherein R4 is methyl, also known as crotonic acid, 7.0 g, 81.3 millimoles (mmol)), then add dropwise cyclohexene (compound (1) wherein R1 to R3a is H, 8.23 mL, 81.3 mmol). The resulting reaction mixture turns bright orange. Mechanically stir the reaction mixture at 70° C. for 3.5 hours. Pour the resulting dark brown thick reaction mixture onto ice/water. Extract the mixture three times with diethyl ether (3×60 mL). Combine the organic layers with saturated aqueous sodium bicarbonate (100 mL), and stir for 20 minutes until bubbling subsides. Separate the organic layer, and wash with saturated bicarbonate (2×60 mL), then brine (60 mL). Dry over magnesium sulfate, and filter. Remove the solvent in vacuo to give 7.2 g of compound (3-1) as a dark brown liquid (60% yield). Purify the compound (3-1) by distillation under reduced pressure (b.p. 75-85° C./5 mm Hg) to give compound (3-1) as a colorless liquid. $^1$H-NMR (400 MHz, CDCl$_3$) δ 2.78-2.63 (m, 1H), 2.56 (ddd, 1H), 2.45-2.29 (m, 1H), 2.21-1.98 (m, 3H), 1.90 (dd, 1H), 1.82-1.38 (m, 4H), 1.11 (d, 3H).

Inventive Example 2: synthesis of compound (3-1) using P$_2$O$_5$/H$_3$CSO$_3$H mixture: compound (3) wherein R1 to R3a is H and R4 is methyl. In the fume hood, under a nitrogen atmosphere in a 250 mL round bottom flask equipped with a stir bar, add (E)-2-butenoic acid (compound (2) wherein R4 is methyl, 10 g, 116 mmol), then add cyclohexene (compound (1) wherein R1 to R3a is H, 9.6 mL, 116 mmol). Cool the reaction mixture to 0° C. Next, add dropwise P$_2$O$_5$/H$_3$CSO$_3$H mixture (0.1/1) (55.3 mL, 348 mmol) at 0° C. Warm up the reaction mixture with stirring to room temperature, and then continue stirring for 20 hours. Dilute the resulting crude product with 50 mL of water. Add solid NaHCO$_3$ until bubbling subsides and the pH of the reaction mixture reaches pH 8 to pH 9. Separate the aqueous and organic layers in a separatory funnel. Extract the aqueous layer three times with diethyl ether (3×50 mL). Combine the organic layers, and wash with brine (50 mL). Dry over magnesium sulfate and filter. Remove the solvent in vacuo to give 13.1 g compound (3-1) as a dark brown liquid product (75% yield). Purify compound (3-1) by distillation at reduced pressure (b.p. 75-80° C./1.75 mm Hg) to give compound (3-1) as a colorless liquid. $^1$H-NMR (400 MHz, CDCl$_3$) δ 2.79-2.65 (m, 1H), 2.60 (ddt, 1H), 2.48-2.32 (m, 1H), 2.22-2.02 (m, 3H), 2.02-1.88 (m, 1H), 1.82-1.44 (m, 4H), 1.14 (d, 3H).

Inventive Example 3: synthesis of compound (4-1): compound (4) wherein R1 to R3a is H and R4 and R5 are methyl. Under an atmosphere of dry nitrogen, weigh out the compound (3-1) of Inventive Example 1 (20.4 g, 135.6 mmol) in a 500 mL round bottom flask, and dissolve in anhydrous diethyl ether (245 mL). Cool the reaction mixture to −78° C. Add dropwise methyl lithium (1.6 M, 110 mL, 176.3 mmol), and stir the solution for 15 minutes at −78° C. Stir the reaction mixture for 20 hours at room temperature to give a reaction mixture containing compound (4-1). Compound (4-1) was not isolated or characterized by $^1$H-NMR. It may be characterized by GC/MS (EI).

Inventive Example 4: synthesis of compound (5-1): compound (5) wherein R1 to R3a is H and R4 and R5 are methyl. Add aqueous 6 M HCL (67 mL) to the reaction mixture containing compound (4-1) in Inventive Example 3, and hydrolyze with stirring for 20 hours at room temperature. Separate the organic phase. Extract the aqueous layer with diethyl ether (2×50 mL). Combine organic layers, and wash with water (80 mL), then saturated NaHCO$_3$ (80 mL), and then brine (80 mL). Dry the organic layers over magnesium sulfate and filter, Remove the solvent in vacuo to give 18.7 g of compound (5-1) as an orange liquid (93% yield), a mixture of double bond regioisomers. $^1$H-NMR (400 MHz, CDCl$_3$) δ 5.27 (m, 1H), 2.73-1.02 (m, 15H).

Inventive Example 5: synthesis of compound (6-1): compound (6) wherein R1 to R3a is H and R4 and R5 are methyl. In a glove box, in a 475 mL glass jar, dissolve compound (5-1) (7.37 g, 49.7 mmol) in hexanes (140 mL). To the stirred solution add dropwise a solution of n-butyl lithium in hexanes (1.6 M, 46.6 mL, 74.5 mmol). Stir the reaction mixture for 20 hours. Collect the compound (6-1) by vacuum filtration, and wash the resulting solid product with hexanes. Dry under vacuum to give 1.9 g of compound (6-1) as a beige solid (24% yield). $^1$H-NMR (400 MHz, THF-d$_8$) δ 5.06 (m, 1H), 2.39-1.50 (broad series of multiplets, 14H).

Inventive Example 6: synthesis of compound (8-1): compound (8) wherein R1 to R3a and R6 to R10 are H and R4 and R5 are methyl. In drybox in a 950 mL glass jar, slurry compound (6-1) (4.8 g, 31.1 mmol) in 272 mL of anhydrous diethyl ether. To the stirred reaction mixture add (Cp)ZrCl$_3$ (8.12 g, 31.1 mmol, compound (7) wherein R6 to R10 is H)

in small portions, then add 1,2-dimethoxyethane (27 mL). Stir the resulting dark orange reaction mixture for 48 hours at room temperature, filter, and remove the solvent under vacuum to give 10.1 g of compound (8-1) as a dark brown solid (86% yield). $^1$H-NMR (400 MHz, benzene-d$_6$) δ 6.00 (s, 5H), 5.22 (s, 1H), 3.06-2.91 (m, 3H), 2.24-2.06 (m, 2H), 1.86-1.72 (m, 2H), 1.59 (s, 6H), 1.50-1.35 (m, 2H).

Inventive Example 7: compound (9-1): compound (9) wherein R1 to R3a and R6 to R10 are H and R4 and R5 are methyl. In drybox in a 240 mL glass jar, slurry compound (8-1) (3.96 g, 10.5 mmol) in anhydrous diethyl ether (65 mL). To the stirred reaction mixture add dropwise a solution of methyl magnesium bromide (3.0 M, 7.89 mL, 23.7 mmol). Stir the reaction mixture for 20 hours at room temperature. Remove the solvent under vacuum. Dissolve the resulting solid product in hexanes (150 mL) and filter. Remove the hexanes under vacuum to give 2.94 g of compound (9-1) as an amber color oil (84% yield). $^1$H-NMR (400 MHz, benzene-d6) δ 5.90 (s, 5H), 5.18 (s, 1 H), 2.53-2.32 (m, 4H), 1.77 (s, 6H), 1.68-1.49 (m, 4H), −0.14 (s, 6H).

Inventive Example 8 (prophetic): compound (9-2): compound (9) wherein R1 to R3a and R4 to R9 are H and R10 is propyl. In drybox in an 240 mL glass jar, slurry a propylcyclopentadienyl analog of compound (8-1) (10.5 mmol, compound (8) wherein R1 to R3a and R4 to R9 are H and R10 is propyl) in anhydrous diethyl ether (65 mL) made from a propylcyclopentadienyl analog of compound (7-1) that is propylcyclopentadienylzirconium (IV) chloride (compound (7) wherein R6-R9 are H and R10 is propyl, "(PrCp)ZrCl$_3$"). Stir mixture and add dropwise a solution of methyl magnesium bromide (3.0 M, 7.89 mL, 23.7 mmol). Continue stirring for 20 hours at room temperature. Remove solvent under vacuum. Dissolve the resulting solid product in hexanes (150 mL) and filter. Remove hexanes under vacuum to give compound (9-2).

Inventive Example 9: synthesis of compound (3-2) and its oxo/R4 regioisomer using P$_2$O$_5$/H$_3$CSO$_3$H mixture: compound (3) wherein R1, R2, and R3a is H and R3 and R4 are methyl, and its oxo/R4 regioisomer. In a fume hood under a nitrogen atmosphere, in a round bottom flask equipped with a stir bar, add (E)-2-butenoic acid (compound (2) wherein R4 is methyl, 1 g, 11.6 mmol), then add 4-methyl-1-cyclohexene (compound (1) wherein R3 is methyl, 1.4 mL, 11.6 mmol). Next, add 1,2-dimethoxyethane (5.5 mL). Cool the reaction mixture to −20° C. Next, add dropwise P$_2$O$_5$/H$_3$CSO$_3$H mixture (0.1:1) (5.53 mL, 34.8 mmol) at −20° C. Warm up the reaction mixture with stirring to room temperature, and then continue stirring for 20 hours. Dilute the mixture into 50 mL of water and 50 mL of diethyl ether. Add solid NaHCO3 until bubbling subsides. Decant the liquid layer. Separate the aqueous and organic layers. Extract the aqueous layer twice with diethyl ether (2×15 mL). Combine the organic layers, and wash with saturated NaHCO$_3$ (20 mL), then brine (30 mL). Dry over magnesium sulfate and filter. Remove the solvent in vacuo to give 1.45 g of compound (3-2) and its oxo/R4 regioisomer as a light brown oil (76% yield). $^1$H-NMR (400 MHz, CDCl$_3$) δ 4.97 (m, 1H), 2.79-0.78 (broad multiplets, mixture of regioisomers).

Inventive Example 10: (prophetic) polymerization of ethylene using a catalyst prepared from compound (8-1) or (9-1). Use a gas-phase fluidized bed reactor ("Reactor") having a reaction zone dimensioned as 304.8 mm (twelve inch) internal diameter and a 2.4384 meter (8 feet) in straight-side height and containing a fluidized reactor bed of polymer granules. Configure the Reactor with a recycle gas line for flowing a recycle gas stream. Fit the Reactor with gas feed inlets and polymer product outlet. Introduce gaseous feed streams of ethylene and hydrogen together with liquid 1-hexene comonomer below the fluidized reactor bed into the recycle gas line. Control individual flow rates of ethylene ("C2"), hydrogen ("H2") and 1-hexene ("C6") to maintain a fixed 1-hexene comonomer to ethylene monomer composition molar ratio ("C6/C2") from 0.0001 to 0.1 (e.g., 0.0050), a constant hydrogen to ethylene molar ratio ("H2/C2") from 0.0001 to 0.1 (e.g., 0.0020), and a constant ethylene ("C2") partial pressure from 1,000 to 2,000 kilopascals (kPa) (e.g., 1,500 kPa). Measure concentrations of all gases by an in-line gas chromatograph to ensure relatively constant composition in the recycle gas stream. Maintain a reacting bed of growing polymer particles in a fluidized state by continuously flowing a make-up feed and recycle gas through the reaction zone. Use a superficial gas velocity of from 0.4 to 0.7 meter per second (m/sec) (e.g., from 0.49 to 0.67 m/sec, or 1.6 to 2.2 feet per second (ft/sec)). Operate the Reactor at a total pressure of 2,000 to 3,000 kPa (e.g., 2344 to about 2413 kPa, or 340 to about 350 pounds per square inch-gauge (psig)) and at a constant reaction temperature of 85° to 115° C. (e.g., 105° C.). Maintain the fluidized bed at a constant height by withdrawing a portion of the bed at a rate equal to the rate of formation of particulate product. The polymer production rate is in the range of 5 to 20 kg/hour (e.g., 13 to 18 kg/hour. Remove the polymer product semi-continuously via a series of valves into a fixed volume chamber, wherein this removed polymer product is purged to remove entrained hydrocarbons and treated with a stream of humidified nitrogen (N2) gas to deactivate any trace quantities of residual polymerization catalyst.

Inventive Example 10a: pilot plant copolymerization of ethylene and 1-hexene using a catalyst prepared from compound (9-1) in a gas phase fluidized bed reactor to give a poly(ethylene-co-1-hexene) copolymer. Used a gas phase fluidized bed copolymerization of ethylene and 1-hexene to make an ethylene/1-hexene copolymer. Used a gas phase fluidized bed reactor that had a 0.35 meter (m) internal diameter and 2.3 m bed height; a distribution grid; and a fluidized bed composed of polymer granules. Passed fluidization gas through the bed at a velocity of about 0.503 meter per second (m/s; 1.65 feet per second (ft/s)). Exited the fluidization gas from the top of the reactor and passed the exited fluidization gas through a recycle gas compressor and shell-and-tube heat exchanger, having a tube side and a shell side, before feeding the gas back into the reactor below the distribution grid. Maintained a constant fluidized bed temperature of 105° C. by continuously adjusting the temperature of water on the shell side of the shell-and-tube heat exchanger. Fed gaseous feed streams of ethylene, nitrogen and hydrogen together with 1-hexene comonomer into the recycle gas line. Operated the reactor at a total pressure of about 2413 kilopascals gauge (kPa gauge). Vented the reactor to a flare to control the total pressure. Adjusted individual flow rates of ethylene, nitrogen, hydrogen and 1-hexene to maintain gas composition targets. Set ethylene partial pressure at 1520 kilopascals (kPa; 220 pounds per square inch (psi)), while setting the C6/C2 molar ratio to 0.0050 and the H2/C2 molar ratio to 0.0020. Used induced condensing agent (ICA) isopentane. Maintained isopentane concentration at about 8.5 to 9.5 mol %. Measured concentrations of all gasses using an on-line gas chromatograph. Prepared spray-dried methylaluminoxane (sdMAO) according to the method of WO 2018/064044. Fed the sdMAO to a pilot-scale UNIPOL™ polyethylene reactor via a 0.635 cm (¼ inch) inner-diameter injection tube. Also fed a mixture of 0.04 wt % compound (9-1) in isopentane via the same injection tube at a feed rate sufficient to provide a target concentration of Zr per gram of spray-dried MAO. Adjusted feed rates to achieve a targeted polymer production rate in the range of 15 to 20 kg/hour. Maintained the fluidized bed at constant height by withdrawing a portion of the bed at a rate equal to the rate of formation of particulate polymer product. Removed polymer product semi-continuously via a series of valves into a fixed volume chamber. Purged removed polymer product with a nitrogen purge that removed a significant portion of entrained and dissolved hydrocarbons in the fixed volume chamber. After purging, discharged the purged polymer product from the fixed volume chamber into a fiber pack for collection. Further treated the collected polymer product with a small stream of humidified nitrogen to deactivate any trace quantities of residual catalyst and cocatalyst entrained therein.

TABLE 1 polyethylene made using catalyst from compound (9-1).

| Property | Inventive Result |
| --- | --- |
| Catalyst mass balance productivity (wt/wt) | 5,144 |
| Melt index I2 (190 C., 2.16 kg, ASTM D1238-13) | 73.1 grams/10 minutes |
| Density (ASTM D792-13, Method B) | 0.9595 g/cm3 |
| Butyl branching frequency* (BBF, NMR) | 0.62 |
| Number average molecular weight | 12,694 g/mole |
| Weight average molecular weight | 36,856 g/mole |
| Molecular mass dispersity ($M_w/M_n$), $Đ_M$, | 2.90 |
| Melting temperature $T_m$ | 133.26 |

*BBF is the number of butyl branches per 1000 main chain carbon atoms.

As can be seen from Table 1 the polymerization catalyst produced in Inventive Example 7 would have a desired catalytic activity and a resultant polyethylene polymer having a desired molecular weight and degree of ethylene enchainment. The polyethylene polymer produced with Inventive Example 10 beneficially would have a weight average molecular weight (Mw) of greater than 30,000 g/mole. Furthermore, the inventive substituted metallocene catalyst used in Inventive Example 10 would have a desired activity of at least 4,800 pounds polymer/pounds catalyst; and a desirable BBF (Butyl Branching Frequency) of below 1. Thus, the polyethylene polymer of Inventive Example 10 would have a desired degree of ethylene enchainment as evidenced by a corresponding BBF of 0.62.

Inventive Example 11 (prophetic): synthesis of compounds (3-3) wherein R1 is methyl, R2 is 1-methylethyl, R3 and R3a are H, and R4 is H or methyl

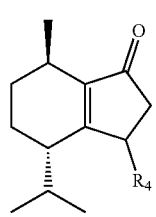

(3-3), and their oxo/R4 regioisomers

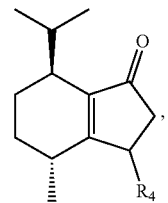

using $P_2O_5/H_3CSO_3H$ mixture: In a fume hood, under a nitrogen atmosphere in a 250 mL round bottom flask equipped with a stir bar, add acrylic acid (compound (2) wherein R4 is H, 116 mmol) or (E)-2-butenoic acid (compound (2) wherein R4 is methyl, 116 mmol), then add (3S,6R)-3-(1-methylethyl)-6-methylcyclohexene (compound (1) wherein R1 is methyl, R2 is 1-methylethyl, R3 and R3a are H, 116 mmol). Cool the reaction mixture to 0° C. Next, add dropwise $P_2O_5/H_3CSO_3H$ mixture (0.1/1) (55.3 mL, 348 mmol) at 0° C. Warm up the reaction mixture with stirring to room temperature, and then continue stirring for 20 hours. Dilute the resulting crude product with 50 mL of water. Add solid $NaHCO_3$ until bubbling subsides and the pH of the reaction mixture reaches pH 8 to pH 9. Separate the aqueous and organic layers in a separatory funnel. Extract the aqueous layer three times with diethyl ether (3×50 mL). Combine the organic layers, and wash with brine (50 mL). Dry over magnesium sulfate and filter. Remove the solvent in vacuo to give a quantity of either compound (3-3) wherein R4 is H or compound (3-3) wherein R4 is methyl, and a quantity of its respective oxo/R4 regioisomer. Purify the compound (3-3) and its oxo/R4 regioisomer by distillation at reduced pressure (1.75 mm Hg) to give purer compound (3-3) and purer oxo/R4 regioisomer. In compound (3-3), the stereochemistry of the carbon atom bonded to R1=methyl is (R) and the stereochemistry to the carbon atom bonded to R2=1-methylethyl is (S). The stereochemistry of the carbon atom bonded to R4 is unspecified. In the oxo/R4 regioisomer, the stereochemistry of the carbon atom bonded to R1=1-methylethyl is (S) and the stereochemistry to the carbon atom bonded to R2=methyl is (R). Stereochemistry of the carbon atom bonded to R4 is unspecified.

Inventive Example 12 (prophetic): synthesis of compound (3-4) wherein R3 and R3a are methyl, R1 and R2 are H, and R4 is methyl, and its oxo/R4 regioisomer, using $P_2O_5/H_3CSO_3H$ mixture: In a fume hood, under a nitrogen atmosphere in a 250 mL round bottom flask equipped with a stir bar, add (E)-2-butenoic acid (compound (2) wherein R4 is methyl, 116 mmol), then add 4,5-dimethyl-1-cyclohexene (compound (1) wherein R1 and R2 are H, R3 is methyl, and R3a is methyl, 116 mmol). Cool the reaction mixture to 0° C. Next, add dropwise $P_2O_5/H_3CSO_3H$ mixture (0.1/1) dropwise (55.3 mL, 348 mmol) at 0° C. Warm up the reaction mixture with stirring to room temperature, and then continue stirring for 20 hours. Dilute the resulting crude product with 50 mL of water. Add solid $NaHCO_3$ until bubbling subsides and the pH of the reaction mixture reaches pH 8 to pH 9. Separate the aqueous and organic layers in a separatory funnel. Extract the aqueous layer three times with diethyl ether (3×50 mL). Combine the organic layers, and wash with brine (50 mL). Dry over magnesium sulfate and filter. Remove the solvent in vacuo to give a quantity of compound (3-4) and a quantity of its oxo/R4 regioisomer. Purify the compound (3-4) and its oxo/R4 regioisomer by distillation at reduced pressure (1.75 mm Hg) to give purer compound (3-4) and purer oxo/R4 regioisomer. Stereochemistries of the carbon atoms respectively bonded to R3, R3a, and R4 are unspecified.

Comparative Example 1: Prepared a polymerization catalyst system in a manner similar to Inventive Example 10a except used a comparative catalyst of same structure as that of compound (9-1) but wherein the comparative catalyst was prepared via a platinum-catalyzed hydrogenation step to convert an indenyl-cyclopentadienyl zirconium dichloride compound to a 4,5,6,7-tetrahydroindenyl-cyclopentadienyl zirconium dichloride compound.

Inventive Example 13: synthesis of compound (8-2): compound (8) wherein R1 to R3a and R6 to R9 are H and R10, R4 and R5 are methyl. In drybox in a 120 mL glass jar, slurry (MeCp)ZrCl3 DME complex (1.0 g, 3.24 mmol) in 30 mL of toluene, and stir. To the stirred reaction mixture add compound (6-1) (0.5 g, 3.24 mmol) in small portions. Stir the resulting reaction mixture for 48 hours at room temperature, filter, and remove the solvent under vacuum to give 1.12 g of compound (8-2) as a light brown solid (89% yield). $^1$H NMR (400 MHz, Benzene-$d_6$) δ 5.85 (t, J=2.7 Hz, 2H), 5.76 (t, J=2.7 Hz, 2H), 5.25 (s, 1H), 3.08-2.97 (m, 2H), 2.22-2.09 (m, 5H), 1.86-1.74 (m, 2H), 1.60 (s, 6H), 1.50-1.39 (m, 2H).

Inventive Example 14: compound (9-2): compound (9) wherein R1 to R3a and R6 to R9 are H and R10, R4 and R5 are methyl. In drybox in a 120 mL glass jar, slurry compound (8-2) (1.07 g, 2.75 mmol) in anhydrous diethyl ether (17 mL). To the stirred reaction mixture add dropwise a solution of methyl magnesium bromide (3.0 M, 2.06 mL, 6.19 mmol). Stir the reaction mixture for 20 hours at room temperature. Remove the solvent under vacuum. Dissolve the resulting solid product in hexanes (30 mL) and filter. Remove the hexanes under vacuum to give 0.6 g of compound (8-1) as an amber color oil (63% yield). $^1$H NMR (400 MHz, Benzene-$d_6$) δ 5.70 (td, J=2.6, 0.6 Hz, 2H), 5.45 (dt, J=4.3, 2.6 Hz, 2H), 5.03 (s, 1H), 2.51-2.24 (m, 4H), 2.09 (d, J=0.6 Hz, 3H), 1.68 (d, J=0.5 Hz, 6H), 1.63-1.42 (m, 4H), −0.27 (s, 6H).

Inventive Example 15: synthesis of compound (3-2) and its oxo/R4 regioisomer using $P_2O_5/H_3CSO_3H$ mixture: compound (3) wherein R1, R2, and R3a is H and R3 and R4 are methyl, and its oxo/R4 regioisomer. In a fume hood under a nitrogen atmosphere, in a round bottom flask equipped with a stir bar, add (E)-2-butenoic acid (compound (2) wherein R4 is methyl, 1 g, 11.6 mmol), then add 4-methyl-1-cyclohexene (compound (1) wherein R3 is methyl, 1.4 mL, 11.6 mmol). Next, add Sulfolane (6 mL). Cool the reaction mixture to −10° C. Next, add dropwise $P_2O_5/H_3CSO_3H$ mixture (0.1:1) (5.53 mL, 34.8 mmol) at −10° C. Keep the reaction mixture at −10° C. for 1 hour. Warm up the reaction mixture with stirring to room temperature, and then continue stirring for 20 hours. Dilute the mixture into 50 mL of water and 50 mL of diethyl ether. Add solid NaHCO3 until bubbling subsides. Decant the liquid layer. Separate the aqueous and organic layers. Extract the aqueous layer twice with diethyl ether (2×15 mL). Combine the organic layers, and wash with saturated $NaHCO_3$ (20 mL), then brine (30 mL). Dry over magnesium sulfate and filter. Remove the solvent in vacuo to give 1.5 g of compound (3-2) and its oxo/R4 regioisomer as a light brown oil (79% yield). $^1$H-NMR (400 MHz, CDCl$_3$) δ 4.97 (m, 1H), 2.79-0.78 (broad multiplets, mixture of regioisomers).

Inventive Example 16: performed dynamic mechanical analysis (DMA) of Inventive Example 10a and Comparative Example 1 using a TA Instruments ARES G2 strain controlled rheometer under Nitrogen gas. A time sweep experiment was performed employing 25 mm parallel stainless steel plates with a gap of approximately 2 mm. The experiment was conducted at a temperature of 190° C. The temperature was controlled at 190° C. using a forced convection oven attachment with Nitrogen as the gas. The sample specimens were loaded onto a fixture at 190° C. and tested at a fixed frequency of 10 rad/sec and 30% strain for 1 hour. Results are shown below in Table 2.

TABLE 2

Results of Dynamic mechanical analysis of Inventive Example 10a and Comparative Example 1.

| Example No. | Initial Complex Viscosity (Pa · s) at time = 0 hour | Final Complex Viscosity (Pa · s) at time = 1 hour | Percent (%) Complex Viscosity Change (time = 1 hour) |
|---|---|---|---|
| Inventive Example 10a | 100.07 | 106.6 | 6.49 |
| Comparative Example 1 | 94.06 | 104.1 | 10.7 |

Pa · s is pascal-seconds.

In Table 2 the polyethylene polymer produced in Inventive Example 10a beneficially has a smaller change of 6.49% in complex viscosity when subjected to dynamic mechanical analysis at a temperature of 190° C. compared to that of the polyethylene polymer produced in Comparative Example 1. Viscosity is directly related to weight average molecular weight (Mw) of the polyethylene polymer, and thus under the test conditions evaluated, Inventive Example 10a has a desired lower change in weight average molecular weight (Mw) at a temperature of 190° C. over 1 hour than does Comparative Example 1. Thus, a polyethylene polymer made in the absence of platinum (e.g., Inventive Example 10a) advantageously has increased molecular weight stability versus a polyethylene polymer made in the presence of platinum (e.g., Comparative Example 1). The inventive method beneficially enables the synthesis of a platinum-free compound (9) (and compound (9) free of other hydrogenation catalyst metals such as Rh, Ru, Ni), which in turns enables the making of platinum-free polyethylene polymer (and polyethylene polymer free of other hydrogenation catalyst metals such as Rh, Ru, Ni).

As discussed earlier, Conia et al., Rand and Dolinski, and others report using PPA or $P_2O_5$/PPA mixture to catalyze a reaction of cycloheptene, cyclohexene, or cyclopentene with an alpha,beta-unsaturated carboxylic acid such as acrylic acid or crotonic acid gives a reaction mixture that contains an ester by-product (e.g., cycloheptyl crotonate, cyclohexyl crotonate, or cyclopentyl crotonate, respectively). We found that using a sulfonic acid reagent ($P_2O_5/H_3CSO_3H$ reagent) to catalyze a reaction of cycloheptene, cyclohexene, or cyclopentene with an alpha,beta-unsaturated carboxylic acid such as acrylic acid or crotonic acid gives a reaction mixture that does not contain an ester by-product (e.g., the reaction does not yield cycloheptyl crotonate, cyclohexyl crotonate, or cyclopentyl crotonate, respectively). We base this finding on analysis of at least one of the reaction mixtures by GC/MS (EI), which fails to show any ester by-product. We also base this finding on seeing that the reaction of cycloheptene, cyclohexene, or cyclopentene with an alpha,beta-unsaturated carboxylic acid such as acrylic acid or crotonic acid in the presence of the $P_2O_5/H_3CSO_3H$ reagent goes much faster than a reaction of cycloheptyl crotonate, cyclohexyl crotonate, or cyclopentyl crotonate, respectively, in the presence of the $P_2O_5/H_3CSO_3H$ reagent.

Without wishing to be bound by theory, we believe that the $P_2O_5/H_3CSO_3H$ reagent reacts with the alpha,beta-unsaturated carboxylic acid (e.g., crotonic acid) to give in situ a mixed anhydride of general formula $R4CH=CHC(=O)—O—SO_2—CH_3$, which generates in situ an acylium ion (i.e., acyl carbonium ion) of formula $R4CH=CHC^+(=O)$, which rapidly undergoes a Friedel-Crafts acylation of cycloalkene to give in situ a ketone of formula $R^{\underline{a}}—C(=O)—R^{\underline{e}}$, wherein $R^{\underline{a}}$ is $R4CH=CH—$ and $R^{\underline{e}}$ is cycloalken-1-yl, which ketone undergoes cyclization reaction to give the corresponding cyclopentenone. For example, when the cycloalkene is cyclohexene and the alpha,beta-unsaturated carboxylic acid is crotonic acid, we believe that the $P_2O_5/H_3CSO_3H$ reagent reacts with the crotonic acid to give in situ a mixed anhydride of general formula $H_3CCH=CHC(=O)—O—SO_2—CH_3$, which generates in situ an acylium ion (i.e., acyl carbonium ion) of formula $H_3CCH=CHC^+(=O)$, which rapidly undergoes a Friedel-Crafts acylation of cycloalkene to give in situ a ketone of formula $R^{\underline{a}}—C(=O)—R^{\underline{e}}$, wherein $R^{\underline{a}}$ is $H_3CCH=CH—$ and $R^{\underline{e}}$ is cyclohexen-1-yl, which ketone undergoes cyclization reaction to give the cyclopentenone that is 2,3,4,5,6,7-hexahydro-3-methyl-1H-inden-1-one (i.e., 7-methyl-bicyclo[4.3.0]-7-nonen-9-one). Therefore, using the $P_2O_5/H_3CSO_3H$ reagent in reaction of a cycloalkene such as cycloheptene, cyclohexene, or cyclopentene with an alpha,beta-unsaturated carboxylic acid such as acrylic acid or crotonic acid does not inherently make the ester by-product (e.g., cycloheptyl crotonate, cyclohexyl crotonate, or cyclopentyl crotonate, respectively) reported by Conia et al., Rand and Dolinski, and others using PPA or $P_2O_5$/PPA mixture.

The invention claimed is:

1. A method of synthesizing a zirconocene dichloride complex of formula (8):

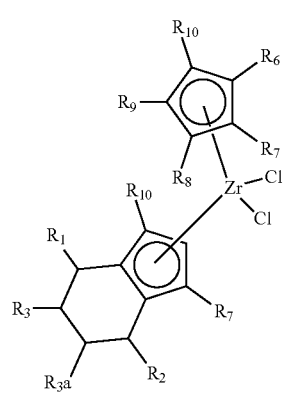

("compound (8)") and/or its R5/R4 regioisomer, the method comprising synthesizing the compound (8) and/or its R5/R4 regioisomer according to steps (A) to (E):

(A) contacting a compound of formula (1) ("compound (1)"):

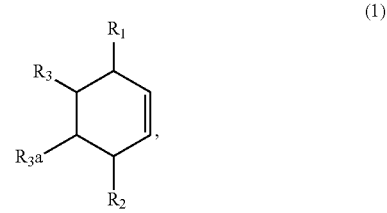

wherein R1, R2, R3, and R3a are independently H or $(C_1$-$C_4)$alkyl, or any two adjacent R1 to R3a groups are bonded together to form a $(C_1$-$C_4)$alkylene and each of the remaining groups of R1 to R3a independently is H or $(C_1$-$C_4)$alkyl, with a compound of formula (2) ("compound (2)"):

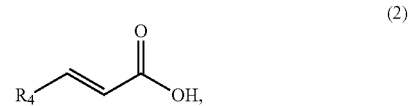

wherein R4 is H or $(C_1$-$C_4)$alkyl, in the presence of an effective amount of a phosphoric and/or sulfonic acid reagent and under reaction conditions sufficient to make a compound of formula (3) ("compound (3)"):

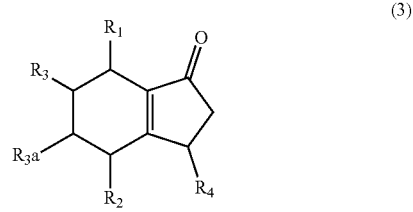

and/or its oxo/R4 regioisomer; wherein R1 to R4 are as defined above; and with the proviso that when each of R1 to R3a is H and R4 is methyl, the phosphoric and/or sulfonic acid reagent and contacting step (A) are free of a polyphosphoric acid (PPA);

(B) contacting the compound (3) and/or its oxo/R4 regioisomer with either a hydride-functional reducing agent or a $(C_1$-$C_4)$alkyl lithium, under reaction conditions sufficient to make a compound of formula (4) ("compound (4)"):

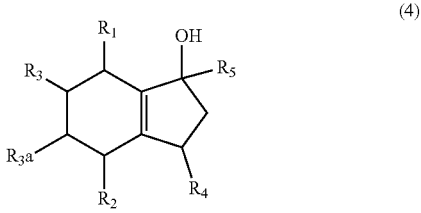

and/or its (HO,R5)/R4 regioisomer, respectively, wherein R1 to R4 are as defined above and R5 is either H or $(C_1$-$C_4)$alkyl, respectively; and (C) contacting the compound (4) and/or its (HO,R5)/R4 regioisomer with dehydration reaction conditions to make a compound of formula (5) ("compound (5)"):

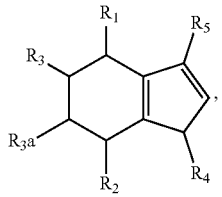
(5)

and/or its R5/R4 regioisomer, respectively; wherein R1 to R5 are as defined above;

(D) contacting the compound (5) and/or its R5/R4 regioisomer with an alkyl lithium under reaction conditions sufficient to make a compound of formula (6) ("compound (6)"):

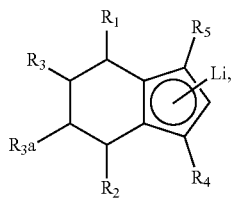
(6)

and/or its R5/R4 regioisomer, wherein R1 to R5 are as defined above; and (E) contacting the compound (6) and/or its R5/R4 regioisomer with a compound of formula (7) ("compound (7)"):

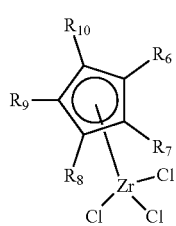
(7)

under reaction conditions sufficient to make the compound (8) and/or its R5/R4 regioisomer, wherein R1 to R5 are as defined above and each of R6 to R10 is independently H or $(C_1$-$C_4)$alkyl.

2. The method of claim 1 further comprising synthesizing a zirconocene dimethyl complex of formula (9):

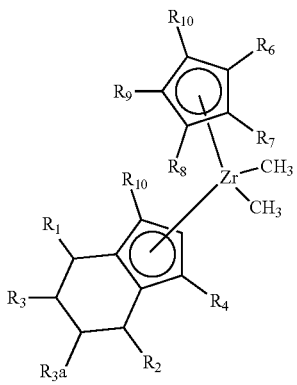
(9)

("compound (9)") and/or its R5/R4 regioisomer, the method comprising synthesizing the compound (8) and/or its R5/R4 regioisomer according to steps (A) to (E) of claim 1; and (F) contacting the compound (8) and/or its R5/R4 regioisomer with an effective amount of methyl magnesium bromide under reaction conditions sufficient to make the compound (9) and/or its R5/R4 regioisomer, wherein R1 to R10 are as defined in claim 1.

3. The method of claim 1, wherein the phosphoric and/or sulfonic acid reagent is a polyphosphoric acid (PPA); a mixture of a phosphorous pentoxide and methanesulfonic acid ("$P_2O_5$/$H_3CSO_3H$ mixture"), or a reaction product of the $P_2O_5$/$H_3CSO_3H$ mixture; or a combination of a PPA and a $P_2O_5$/$H_3CSO_3H$ mixture, or a reaction product of the PPA and the $P_2O_5$/$H_3CSO_3H$ mixture; with the proviso that when each of R1 to R3a is H and R4 is methyl, the phosphoric and/or sulfonic acid reagent and the contacting step (A) are free of the PPA.

4. The method of claim 1 wherein the phosphoric and/or sulfonic acid reagent is a polyphosphoric acid (PPA); with the proviso that at least one of R1 to R3a is $(C_1$-$C_4)$alkyl or R4 is H.

5. The method of claim 1, wherein the phosphoric and/or sulfonic acid reagent is the $P_2O_5$/$H_3CSO_3H$ mixture, or a reaction product of the $P_2O_5$/$H_3CSO_3H$ mixture.

6. The method of claim 1, wherein the phosphoric and/or sulfonic acid reagent is the combination of the PPA and the $P_2O_5$/$H_3CSO_3H$ mixture, or a reaction product of the PPA and the $P_2O_5$/$H_3CSO_3H$ mixture.

7. The method of claim 1, characterized by any one of limitations (i) to (ix): (i) wherein at least one of R1 to R3a is a $(C_1$-$C_4)$alkyl or R4 is H; (ii) wherein each of R1 to R4 is H; (iii) wherein each of R1 to R3a is H and R4 is methyl; (iv) wherein in compound (1) each of R1, R2, and R3a is H and R3 is methyl; in compound (2) R4 is methyl; and in compound (3) each of R1, R2, and R3a is H and each of R3 and R4 is methyl; and in its oxo/R4 regioisomer each of R1, R2, and R3 is H and each of R3a and R4 is each methyl; (v) wherein R1 and/or R2 is methyl and R3 and R3a is H; (vi) wherein R1 is methyl, R2 is 1-methylethyl (i.e., isopropyl), and R3 and R3a are H; (vii) wherein R1 is 1-methylethyl (i.e., isopropyl), R2 is methyl, and R3 and R3a are H; (viii) wherein R1 and R2 independently are $(C_1$-$C_4)$alkyl, R3 and R3a are H, and the stereochemistry of the carbon atom bonded to R1 is (R) and the stereochemistry to the carbon atom bonded to R2 is (S); and (ix) wherein R1 and R2 independently are $(C_1$-$C_4)$alkyl, R3 and R3a are H, and the stereochemistry of the carbon atom bonded to R1 is (S) and the stereochemistry to the carbon atom bonded to R2 is (R).

8. The method of claim 2 further comprising polymerizing an olefin, the method comprising contacting ethylene and/or an alpha-olefin with a catalyst made by contacting the compound (8) or (9), or its R5/R4 regioisomer, made by the method of claim 2, with an activator, under conditions sufficient to make a polyolefin polymer comprising a polyethylene homopolymer, an ethylene/alpha-olefin copolymer, or a poly(alpha-olefin) homopolymer.

9. The method of claim 1 wherein the compound (4) or its (HO,R5)/R4 regioisomer is free of platinum, palladium, nickel, rhodium, and ruthenium.

* * * * *